(12) United States Patent
Workman et al.

(10) Patent No.: US 8,140,500 B2
(45) Date of Patent: Mar. 20, 2012

(54) SPECTRAL MEASUREMENT WITH ASSISTED DATA ANALYSIS

(75) Inventors: Jerome J. Workman, Madison, WI (US); Stephen R. Lowry, Madison, WI (US); Nicholas Simon Nunn, Verona, WI (US); Kathleen J. Schulting, Oregon, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 1201 days.

(21) Appl. No.: 11/725,097

(22) Filed: Mar. 16, 2007

(65) Prior Publication Data

US 2007/0233401 A1   Oct. 4, 2007

Related U.S. Application Data

(60) Provisional application No. 60/783,366, filed on Mar. 17, 2006.

(51) Int. Cl.
*G06F 7/00* (2006.01)
*G06F 17/30* (2006.01)

(52) U.S. Cl. ............ 707/705; 707/749; 702/27; 702/28; 702/104

(58) Field of Classification Search .................. 356/301, 356/328, 326; 702/20, 27, 28, 104; 707/769, 707/803, 780, 705, 749
See application file for complete search history.

(56) References Cited

U.S. PATENT DOCUMENTS

| | | | |
|---|---|---|---|
| 5,519,219 A | 5/1996 | Alexay et al. | |
| 5,714,758 A | 2/1998 | Neu | |
| 6,441,375 B1 | 8/2002 | Joseph et al. | |
| 6,546,146 B1 | 4/2003 | Hollinger et al. | |
| 6,560,546 B1 | 5/2003 | Shenk et al. | |
| 6,767,732 B2 | 7/2004 | Alocilja et al. | |
| 6,820,013 B1 | 11/2004 | Frickel et al. | |
| 6,900,734 B2 | 5/2005 | Duan | |
| 6,937,323 B2 | 8/2005 | Worthington et al. | |
| 6,985,216 B2 | 1/2006 | Treado et al. | |
| 7,072,770 B1 | 7/2006 | Schweitzer et al. | |
| 7,084,972 B2 | 8/2006 | Treado | |
| 7,117,103 B2 | 10/2006 | Szelewski et al. | |
| 7,161,672 B2 | 1/2007 | Gornushkin et al. | |
| 7,194,369 B2 * | 3/2007 | Lundstedt et al. | ............ 702/104 |
| 2003/0162221 A1 | 8/2003 | Bader et al. | |
| 2005/0289166 A1 * | 12/2005 | Stanley et al. | ................ 707/100 |
| 2006/0031486 A1 | 2/2006 | Miner | |
| 2007/0026426 A1 * | 2/2007 | Fuernkranz et al. | ............ 702/20 |

OTHER PUBLICATIONS

"Chemical Abstracts Plus database search results for patents using the terms 'spectroscopy and 'computer network'", Mar. 16, 2007.

* cited by examiner

*Primary Examiner* — Vincent Boccio
(74) *Attorney, Agent, or Firm* — Michael C. Staggs; DeWitt Ross & Stevens

(57) ABSTRACT

A system is provided wherein spectrometer measurements, and/or measurements from other analytical instruments, are transmitted to a processing station which determines the component substances of the sample(s) subjected to the measurements. The names of the component substances are then inserted into database search queries related to matters such as handling precautions, causes/sources of the substances, remedies and neutralizing agents for the substances, regulations related to the substances, etc. The results of the search queries are then provided to the personnel who made the measurements, preferably wirelessly and almost immediately after the measurements were made. The system therefore provides nearly immediate guidance as to what substances are present and how to handle them, which can be useful for inexperienced personnel in hazardous response, contraband detection, industrial process control, and other situations.

15 Claims, 2 Drawing Sheets

US 8,140,500 B2

SPECTRAL MEASUREMENT WITH ASSISTED DATA ANALYSIS

CROSS-REFERENCE TO RELATED APPLICATIONS

This application claims priority under 35 USC §119(e) to U.S. Provisional Patent Application 60/783,366 filed 17 Mar. 2006, the entirety of which is incorporated by reference herein.

FIELD OF THE INVENTION

This document concerns an invention relating generally to usage of analytical instruments to acquire measurements in the field, and more specifically to rapid interpretation and analysis of spectrometry measurements attained in the field.

BACKGROUND OF THE INVENTION

Portable molecular spectrometers are occasionally used to identify the characteristics of gas, liquid, and solid samples. In these spectrometers—which are exemplified by the spectrometers in U.S. Pat. No. 7,084,972 to Treado, U.S. Pat. No. 6,985,216 to Treado et al., U.S. Pat. No. 6,900,734 to Duan, U.S. Pat. No. 5,714,758 to Neu, and U.S. Pat. No. 5,519,219 to Alexay—light is directed at a sample, and the light reflected from, scattered by, and/or transmitted through the sample is then picked up by a photosensitive detector to be analyzed for changes in wavelength. These changes can then provide information regarding the composition of the sample, its chemical bonds, and other features. Portable spectrometers would seem to provide an extremely useful tool for a variety of applications, such as for law enforcement (e.g., to identify a suspected narcotic substance), homeland security (e.g., to identify a suspected explosive), hazardous materials response (e.g., to identify matter suspected of being toxic or explosive), manufacturing/process testing (e.g., to verify content of, and/or contaminants in, foodstuffs, pharmaceuticals, or other goods), and similar applications. However, without extensive training, it is often difficult to interpret the readings returned by the spectrometers—for example, to determine the composition of a sample being tested. Further, even if one can correctly interpret the spectrometer readings, further expertise is needed to determine how to respond to these readings. To illustrate, even if the user knows that some substances X, Y, and Z are present in a sample, if the user is unfamiliar with one or more of these substances, the user may not know what to make of the readings: the user may need information on toxicity, volatility, handling precautions, environmental ramifications, and common uses and occurrences (e.g., substance X is an byproduct arising from certain industrial processes, substances Y and Z indicate certain conditions when encountered together, selected ones of substances X, Y, and Z are commonly used to mask the presence of prohibited substances, and so forth). As a result, substantial delays can be encountered as the user attempts to seek further information and guidance, and/or as the sample is forwarded to a laboratory for more extensive testing and expert analysis. These delays can lead to substantial costs and risks in both commercial and governmental settings.

SUMMARY OF THE INVENTION

The invention involves methods and systems which are intended to at least partially solve the aforementioned problems. To give the reader a basic understanding of some of the advantageous features of the invention, following is a brief summary of preferred versions, with reference being made to the accompanying drawings. Since this is merely a summary, it should be understood that more details regarding the preferred versions may be found in the Detailed Description set forth elsewhere in this document. The claims set forth at the end of this document then define the various versions of the invention in which exclusive rights are secured.

An exemplary system for providing user-friendly molecular spectrometry measurement and analysis, with decreased need for expertise and assistance in interpreting measurement results, is schematically depicted in FIG. 1. Exemplary steps in the operation of the system of FIG. 1 are then illustrated in FIG. 2. Referring to FIG. 1, a data capture unit 100—shown as a pistol-type hand-held unit—bears a sensor 102 allowing the unit to capture wavelength data from a sample adjacent the data capture unit 100, with the wavelength data being exemplified by a conventional spectrum 120, i.e., a set of light intensity vs. wavelength data. This step of capturing sample data with the sensor 102 is also depicted in FIG. 2 at step 200. The sensor 102, which may assume a variety of forms, is depicted in FIG. 1 as a photosensitive detector which captures light from a sample, with the light incident on the sample originating from an adjacent emitter 104. The data capture unit 100 also preferably includes a display 106 for visually presenting data to the unit's user, e.g., an LCD display; a camera 108 capable of capturing one or more images of the sample; and a transmitter 110 (most preferably a wireless transmitter) for transmitting sample wavelength data, camera images, and/or other data to a processing station 130, to be discussed below. It is also useful if the data capture unit 100 includes a receiver 112 for receiving data from the processing station 130 or from other sources, with the receiver 112 here being depicted as a wireless receiver provided with the wireless transmitter 110. As will be discussed below, once the data capture unit 100 receives data from the processing station 130 or elsewhere, the unit 100 may process the data and provide related output on the display 106.

The processing station 130, which is depicted in FIG. 1 as an electronic workstation such as a personal computer, is in communication with a network of databases 140 wherein at least some of the databases 140 contain information about the properties of substances. The processing station 130 is configured to receive the sample data from the sensor 102 (preferably wirelessly, as by the wireless receiver 132), and to process the sample data and generate substance data which at least partially identifies one or more substances within the sample (step 202 in FIG. 2). As an example, where the sample data contains wavelength data such as spectra, the processing station 130 may include a database of reference spectra against which the sample data may be matched or "fingerprinted," with matches indicating candidate substances that may be present in the sample. The substance data generated by the processing station 130 is preferably provided in the form of discrete words/strings reflecting the names of the substances/chemicals, moieties/functional groups, structures, or mixtures thereof present in the sample.

The processing station 130 is configured to generate one or more search queries from the substance data (step 208 in FIG. 2), and to deliver these search queries to the networked databases 140 (step 210 in FIG. 2). This can be done by simply taking the substance data and adding one or more "Essential Discrete Words" (EDWs)—discrete words/strings relating to some topic of interest—to the substance data, and using the resulting strings as the search query/queries. For example, if the analysis of the sample data by the processing station 130 indicates the possible presence of substances X, Y, and Z, the processing station 130 can generate search queries for each by (for example) adding one or more of the EDWs "IUPAC" (the acronym for the International Union of Pure and Applied Chemistry, which assigns standards for the naming of substances); "CAS" (the acronym for the Chemical Abstracts Service, which maintains collections of information about substances); "MSDS" (the acronym for Material Safety Data Sheet, a standard form containing information regarding the properties of a substance); "formula"; "properties"; "standard"; "reference"; "uses"; "suppliers"; "commercial"; "trade name"; "toxicity"; "hazard"; "measurement"; "regulation"; "ultraviolet spectrum"; "near infrared spectrum"; "infrared spectrum"; "Raman spectrum"; "NMR spectrum"; "microwave spectrum"; "terahertz spectrum"; and other such terms which are likely to, in connection with the substance name, return information regarding the properties, uses, handling/disposal, regulation, etc. of the substance in question.

Some or all of the search queries may be directed only to particular databases and/or websites 140. For example, search queries for "X MSDS," "Y MSDS," etc. could be directed only to MSDS databases, or only to websites containing MSDS databases, as by restricting the search to certain predefined website addresses stored within the processing station 130. Alternatively, search queries could be addressed to all databases 140 available to or catalogued by the processing station 130. For example, search queries for "suppliers X," "suppliers Y", etc. could simply be inserted by the processing station 130 into a commercially available World Wide Web search engine, such as Google (Google, Inc., Mountain View, Calif., USA), so that (presumably) current information about the commercialization of substances X, Y, etc. can be gathered.

Richer and potentially more relevant information can be obtained if search query terms are combined, if searches are recursive, and/or if the search queries are also provided to one or more human experts as well as to the networked databases 140. Regarding the combination of search query terms, this is particularly useful with substance names. If search queries include combinations of the substances X, Y, and Z—as by searching for "X Y Z," "X Y," "X Z," "Y Z," etc.—the search query results may include information which is highly relevant to the sample in question. For example, substances X, Y, and Z may by themselves be relatively common, inert, and uncontroversial, but when combined they may indicate the presence of harmful materials or conditions, contraband, or some other situation requiring attention.

As for the option of recursive searching, if the results of one search query are filtered and then used for a subsequent search query, the system may be able to more rapidly collect relevant information. For example, if the processing station 130 first submits the search query "IUPAC X" to the networked databases 140 to thereby receive the standard chemical name(s) of substance X in the search query results, and the processing station 130 then uses the standard chemical name(s) in subsequent search queries (either individually and/or in combination with each other, and/or with the additional search terms noted previously, e.g., "CAS," "MSDS," etc.), the returned search query results may have greater relevance because the name of substance X has been "standardized" prior to further searching.

As for the option of submitting the search queries to human experts as well as to the networked databases 140, parties skilled in the topic of field measurements, and/or in topics such as hazardous materials safety, counterfeit/narcotics detection, etc., can also be in networked communication with the processing station 130. These experts can receive the sample data and/or search queries (as illustrated by step 212 in FIG. 2), and can then provide their feedback and suggestions to the processing station 130, which may compile the expert feedback along with the search query results from the networked databases 140. In this case, it can be particularly helpful if the data capture unit 100 includes a camera 108 which captures images of the sample, with the images being transmitted to the processing station 130 and in turn to the experts, so that the experts can review the sample data in the context of its environment.

The returned search query results (the returned files/webpages, file/webpage lists, expert feedback, etc.) can then be collected by the processing station 130. Preferably, these search query results are restricted in number, as by collecting only some limited number of the returned files/webpages (such as the "top five" responses to each search query) and/or by eliminating duplicative results. Additionally or alternatively, the search query results may be filtered for relevance, as by discarding certain of the returned files/webpages if they contain certain terms (such as "advertisement"), or conversely by retaining returned files/webpages only if they contain certain terms, such as one or more of the terms noted above (e.g., "CAS," "MSDS," etc.). These steps are illustrated by step 214 in FIG. 2.

After the search query results are collected (and preferably restricted and filtered) by the processing station 130, they may be compiled/organized into a standard format, as by segregating the results of the search queries from each other with appropriate headings (as shown by step 216 in FIG. 2). For example, the search query results for the query "CAS X" can be presented under the heading "CAS X," followed by the heading "MSDS X" above the compiled results for the search query "MSDS X," followed by the heading "uses X" above the compiled results for the search query "uses X," and so forth. At least some of these search query results may then be transmitted to the data capture unit 100 (preferably wirelessly), and may be visually provided to the user on the display 106, thereby providing the user with information relating to the properties of the substances to which the captured sample data relate. The user is then in a better position to make speedy decisions about the sample in the field or elsewhere, without the need to wait for laboratory results and/or further guidance.

Further advantages, features, and objects of the invention will be apparent from the remainder of this document in conjunction with the associated drawings.

DETAILED DESCRIPTION OF PREFERRED VERSIONS OF THE INVENTION

Figure 1:
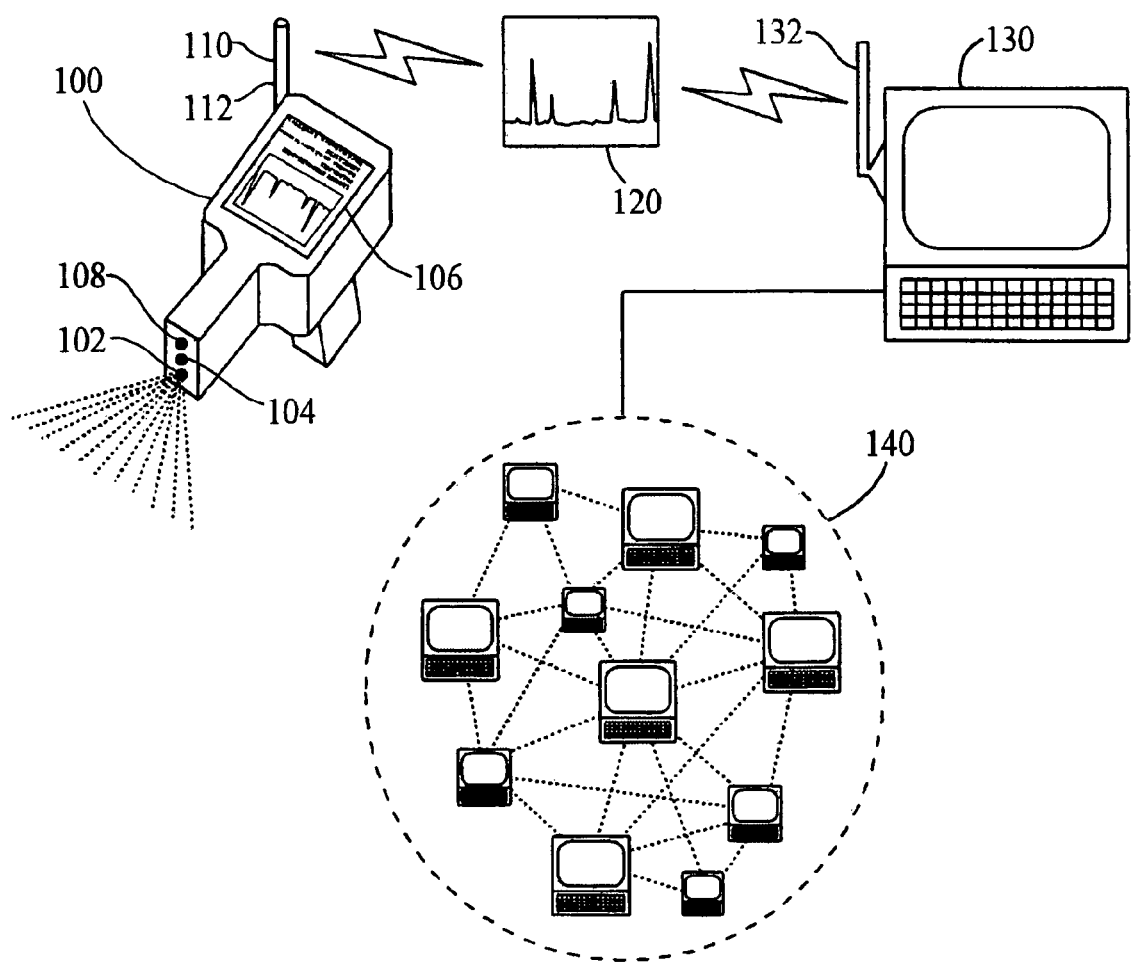
FIG. 1 is a simplified schematic depiction of components of an exemplary version of the system.

To review the exemplary version of the invention discussed above in greater detail, it should initially be understood that the data capture unit 100 depicted in FIG. 1 is merely exemplary, and the data capture unit 100 can assume a wide variety of forms different from the one shown. As an example, a data capture unit 100 could include multiple sensors 102 having the same or different sensitivities, measurement ranges, property measurement capabilities, and so forth. To illustrate, the data capture unit 100 of FIG. 1 might include multiple detectors 102 configured to capture spectra in the infrared (IR), near infrared (NIR), ultraviolet (UV-Vis), Raman, and other ranges using Fourier Transform (FT) or other analysis techniques. As another example, while the data capture unit 100 as shown is configured to capture sample data via a diffuse reflectance mode of measurement (i.e., light is emitted from an emitter/light source 104, and the light scattered by an adjacent sample is then collected by the detector 102), the data capture unit 100 may be configured to allow the unit to capture sample data via other modes, such as transmittance (wherein the detector 102 is situated opposite the emitter 104, so that light transmitted through a sample is captured); transreflectance (wherein light from the emitter 104 travels through the sample, strikes a mirror, and then travels back through the sample to be captured at a detector 102); and so forth. As a final example, some or all of the sensors 102 on the data capture unit 100 could be other than molecular spectrometry sensors 102, e.g., the data capture unit 100 might include mass spectrometers, gas chromatographs, magnetic resonance instruments, radiation detectors 102, or other measurement devices. In all cases, the overall objective of the system would be to identify candidate substances within one or more samples, and to communicate information to the user regarding the substances, e.g., their uses, consequences, handling, etc., so that the user might better know how to proceed with the sample.

Additionally, the data capture unit 100 need not be provided in a single discrete unit, and it might be formed of several components which are combined to provide the desired functionality. To illustrate, the data capture unit 100 could be provided by one or more sensors 102 which bear an interface which communicates with a personal digital assistant, mobile telephone, or similar device which has wireless communications capability for sending and receiving communications (e.g., sample data) to and from the processing station 130. In this respect, it is notable that since many mobile telephones and personal digital assistants include cameras for capturing images, and/or wireless location features (such as Global Positioning) for placing the location of these devices, these devices may provide any image capture functionality and/or location-stamping functionality desired for the data capture unit 100. As will be discussed below, if such devices have sufficient processing power, they might also execute some of the functionality previously discussed as being performed by the processing station 130, e.g., they might analyze the sample data to identify candidate substances within the sample.

Further, the data capture unit 100 need not be portable, nor need it communicate wirelessly with the processing station 130. To illustrate these possibilities, the data capture unit 100 might be provided as a series of sensors 102 distributed along a fence line or the like, which can be useful for detecting fugitive emissions from a facility or otherwise monitoring the boundaries of the facility. Each sensor 102 might bear a "tangible" communications channel to the processing station 130, e.g., a wired and/or optical fiber connection.

The sample data captured by the sensor(s) 102 may have varying degrees of complexity. For example, where molecular spectrometry sample data are concerned, the sample data may take the form of zero order data (e.g., the data may represent light intensity/amplitude at a single wavelength); first order data (e.g., amplitudes/intensities at multiple wavelengths, as exemplified by the sample data 120 shown in FIG. 1); second order data (e.g., amplitudes/intensities at multiple wavelengths over time, or amplitude/intensity at a single wavelength but at multiple XY Cartesian locations); or higher order data (e.g., data which vary in additional ones of the dimensions of amplitude/intensity, frequency, XYZ Cartesian space, and/or time). It should be understood that the data capture unit 100 and/or the processing station 130 may need to convert data of the second order and higher into several sets of first order data because many reference libraries are configured for matching/fingerprinting of first order data.

To assist with recordkeeping, sample data captured by the data capture unit 100 is preferably stored at the processing station 130 (or on the data capture unit 100 itself) in conjunction with identifying data such as date and time stamps, the location at which the sample data was captured (which might be provided via GPS and/or RFID location technology built into the data capture unit 100), the identity of the user, images captured from the camera 108, and so forth.

The database network 140 can range in size from a small and private local area network having a centralized server, to a large and public wide area network having distributed servers (such as the World Wide Web). It can also include a variety of networks ranging in size and organization (i.e., distributed versus centralized servers). It is contemplated that the network of databases 140 will often take the form of a local area network connecting computers/databases within a laboratory facility, government agency, or the like, along with a wide area network connecting computers/databases across the laboratories and offices of distant laboratories, universities, and professional societies, as well as connecting the system to the World Wide Web.

Figure 2:
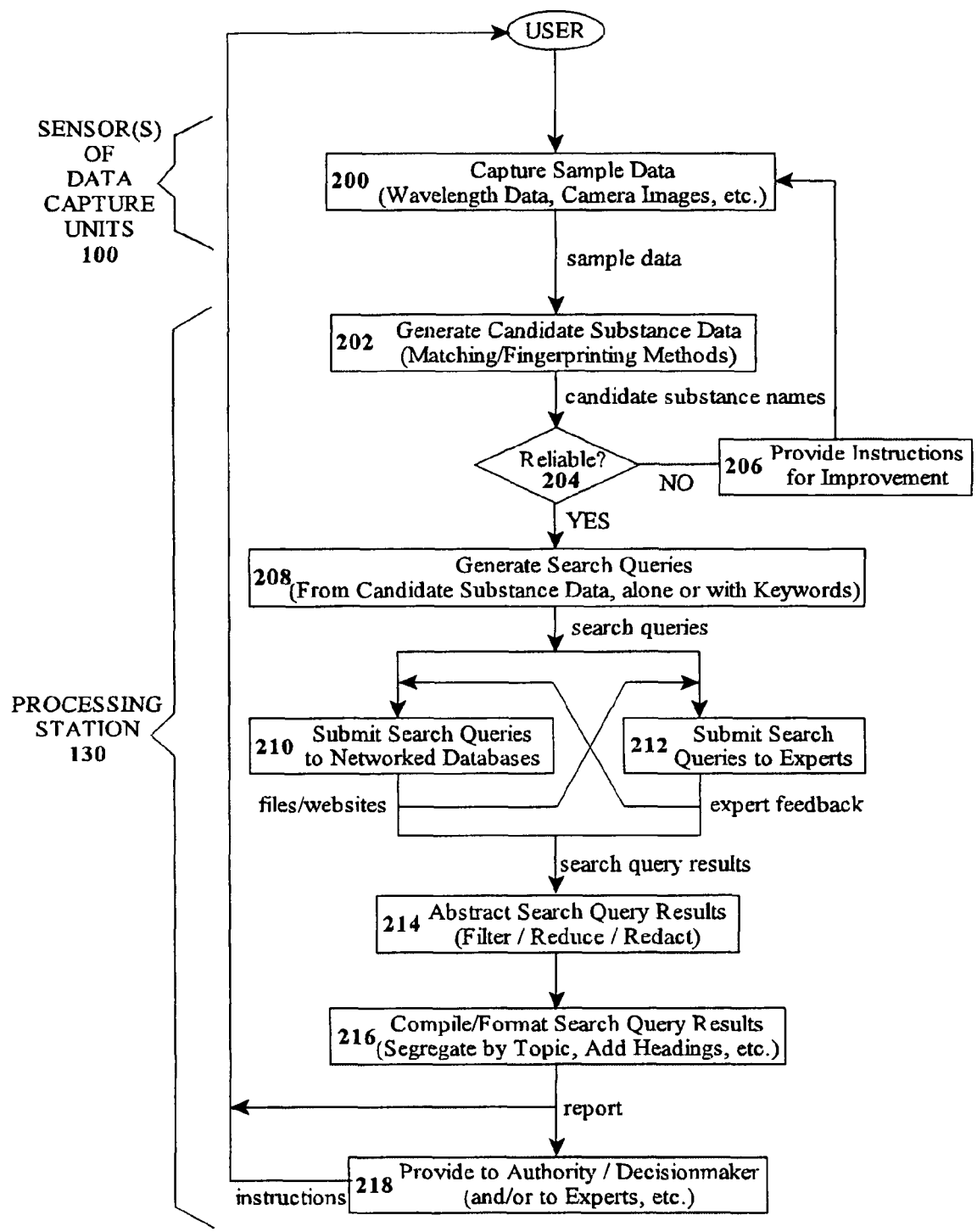
FIG. 2 is a process flow diagram illustrating steps that may occur during the operation of the exemplary system of FIG. 1.

The processing station 130 preferably takes the form of a personal computer equipped with software for comparing captured sample data with reference spectra or other reference data, and identifying the substances within the samples via "fingerprint comparison" or similar matching methods (step 202 in FIG. 2). To illustrate, reference spectra (spectra captured from known substances) are available for comparison with sample spectra, whereby close correspondence between the reference spectra and sample spectra can indicate correspondence between substances. Exemplary spectral libraries, as well as matching/fingerprinting software, are available from Thermo Fisher Scientific, Inc. (Waltham, Mass., USA) and from the U.S. National Institute of Standards and Technology (Gaithersburg, Md., USA). Additionally, a variety of matching/fingerprinting techniques are described in the literature, e.g., in U.S. Pat. No. 7,072,770 to Schweitzer et al., as well as U.S. Pat. No. 7,161,672 to Gornushkin et al., U.S. Pat. No. 7,117,103 to Szelewski et al., and U.S. Pat. No. 6,767,732 to Alocilja et al. Since a wide variety of reference libraries and matching/fingerprinting methodologies are available, it should be understood that the processing station 130 might utilize multiple libraries and multiple matching methodologies, and may compare results from different libraries and methodologies to verify the identities of candidate substances within the sample to a higher level of confidence. It should also be understood that some or all reference libraries, and some or all matching/fingerprinting functionality, need not be present at the processing station 130 itself. For example, the processing station 130 may be in networked communication with reference library databases 140, and it may issue the captured sample data as a search query to these networked reference library databases 140. The processing station 130 may then collect the search results, which include one or more candidate substance names, for compilation, verification and confidence level checking, and similar steps before generating a final list of candidate substances within the sample.

Since the usefulness of the later search query results is limited if the system does not properly identify the candidate substances within the sample, it is recommended that the matching/fingerprinting system provide information to the user regarding the reliability of its matching/fingerprinting efforts (step 204 in FIG. 2). To illustrate, if the processing station 130 is unable to determine candidate substances within the sample to some predetermined degree of confidence—one that is perhaps set by the user in accordance with the importance of the tasks on which the user is working—it might return a message to the user if the identification of one or more of the candidate substances is questionable.

Additionally or alternatively, one or more steps can be taken to attempt to attain higher confidence (step 206 in FIG. 2). Initially, the processing station 130 might provide suggestions to the user to obtain more reliable/definite sample data, and/or might even upload new software/firmware to the data capture unit 100 to enable higher-quality sample data to be captured. As examples, such instructions or uploads might relate to adjusting the exposure time (the time during which the detector 102 captures light from the sample); capturing multiple exposures which might be subsequently averaged (which can reduce background noise and measurements); adopting new signal processing algorithms; and so forth. Alternatively and/or additionally, the user might be instructed that additional modes of measurement can enhance confidence, e.g., capturing of sample data with multiple sensors 102, in different wavelength ranges, and/or in different measurement modes (e.g., different modes of diffuse reflectance, transmittance, transreflectance, etc.). It is possible that the data capture unit 100 might accept instructions for capturing additional sample data with little or no interaction with the user. For example, if the data capture unit 100 bears multiple sensors 102, a first measurement taken by the user might only involve one of these sensors 102. If this first measurement does not allow identification of candidate substances within the sample to a desired degree of confidence, the processing station 130 might have the data capture unit 100 automatically switch to a second and/or subsequent sensors 102 for subsequent measurements, and might instruct the user to take another measurement. This process can be repeated until satisfactory identification occurs.

As another option for enhancing reliable identification of candidate substances within the sample, the invention may include some degree of expert participation in verifying sample measurement reliability, and/or in the identification of the candidate substances. (As discussed previously and shown at step 212 in FIG. 2, such expert participation can also extend to the later generation of search queries including the candidate substance names, and to the processing and analysis of search results.) It is expected that expert participation regarding the quality and reliability of sample data, and/or of the identity of candidate substances therein, will be particularly useful since this information will have a significant impact on the value of the later search query results. As one example, the processing station 130 may be in networked communication with experts at one or more laboratories, government agencies, or other locations at which personnel with experience in field measurements and/or in the issue at hand (e.g., hazardous materials handling, contraband detection, industrial process control, etc.) may monitor sample data taken by data capture units 100 and provide suggestions and instruction. As another example, the user might pay a "subscription fee" to a service bureau to review and provide feedback on the quality of sample data, on the certainty of the candidate substances identified therefrom, on the pertinence of substance name search queries, and/or on the meaning of substance query search results.

As yet another option for attaining more reliable identification of candidate substances within the sample, the processing station 130 might submit one or more initial search queries to the networked databases 140 (and/or to any experts in communication with the system) directed towards obtaining more reliable sample data. As an example, the processing station 130 might compose search queries consisting of the candidate substance names in combination with terms such as "ultraviolet spectrum," "near infrared spectrum," "infrared spectrum," "Raman spectrum," and so forth. The returned search queries, which may contain information on obtaining higher-quality sample data, may then be returned by the processing station 130 to be read by the user on the display 106 so that the user may obtain new sample data before proceeding. As another illustration, it can be useful to simply submit initial search queries consisting of varied combinations of the candidate substance names—for example, if candidate substances X, Y, and Z were tentatively identified, it can be useful to execute searches for "X Y Z," "X Y," "X Z," and "Y Z." The resulting search query results, when reviewed in the context of the sample in question, may allow a user to confidently assume that certain candidate substances are correctly (or incorrectly) identified, as by informing that certain substances are commonly found in combination with others.

Ultimately, regardless of whether the processing station 130 uses only matching/fingerprinting techniques to identify the candidate substances, or whether it also uses one or more of the methods noted above for enhancing the quality of identification, it is useful to have the user (and/or experts) confirm the candidate substances to be searched before further search queries are constructed. It is also useful if the processing station 130 and its matching/fingerprinting system incorporate artificial intelligence with learning capabilities, such that once candidate substances are identified in particular situations with an acceptable degree of certainty, data relating to the identification is stored. In this manner, if the same or similar sample data is later captured under the same or similar circumstances, the processing station 130 can utilize the prior identification of the candidate substances to inform and expedite its identification of later candidate substances.

When the processing station 130 has completed executing the matching/fingerprinting methodology, it should have a list of one or more candidate substances which are believed to be present in the sample, with each candidate substance being identified by the substance name(s) assigned by the reference libraries. This should be understood as encompassing not only chemical names, but also the names of moieties/functional groups, structures, or mixtures thereof, provided the sample data contains information on such matter, and the reference libraries are able to identify and name such matter. It should also be understood that the "names" returned by the matching/fingerprinting methods may not necessarily be standard/conventional names (e.g., IUPAC standard names), and could instead be industry/trade designations, such as CAS numbers, trade names or trademarks, etc. Since these reference libraries do not always implement standard or current naming standards, it can be useful to "standardize" the candidate substance names by searching for the candidate substance names in IUPAC, CAS, and/or tradename/trademark databases 140 so that search queries can be generated not only on the candidate substance name(s), but also any variant/alternative name(s). As discussed previously, this may be done by the processing station 130 via searching for the alternative names amongst the networked databases 140 (and/or experts).

After all alternative/variant names are identified (if such identification is performed), the processing station 130 can then generate search queries directed to obtaining information on uses, hazards, regulation, handling/clean-up procedures, etc. related to the candidate substances, with these search queries being provided to the networked databases 140 and/or experts. This step is illustrated at 208 in FIG. 2. Search queries are preferably generated by the processing station 130 in accordance with the concept of "essential discrete words" (EDWs): the substance names, which are provided in plain-language form as discrete alphanumeric strings/words, are combined with other plain-language discrete strings/words, and the combinations may then be utilized as search queries in conventional database search engines. To illustrate this process, an example follows.

EXAMPLE 1

After the sample data are provided to the processing station 130, the processing station 130 might check spectral reference libraries and find a match with the candidate substances "N-[2-adamantil]-N-[para-bromphenyl]amine" and "Delta4-Androsten-17beta-ol-3-one" (these names being provided by the reference libraries). Initial search queries seeking alternative/variant names might then be generated by the processing station 130 by combining these EDWs with the EDWs "IUPAC" and "trade name" (or "commercial name," "street name," or simply "name" or the like)—for example:

IUPAC N-[2-adamantil]-N-[para-bromphenyl]amine
trade name N-[2-adamantil]-N-[para-bromphenyl]amine
IUPAC Delta4-Androsten-17beta-ol-3-one
trade name Delta4-Androsten-17beta-ol-3-one These search queries may return results from the networked databases 140 and/or experts to the effect that "Delta4-Androsten-17beta-ol-3-one" is also known as "(17)-17-Hydroxyandrost-4-en-3-one," and is commonly referred to as "testosterone" or "testostroval," and also that "N-[2-adamantil]-N-[para-bromphenyl]amine" is commonly referred to as "bromantan."

Once all these candidate names are generated, some or all can be used as EDWs in further search queries, either alone, in combination with each other, and/or in combination with other EDWs. As an example, the processing station 130 could issue the following search queries to the networked databases 140 and/or experts:

testosterone bromantan
uses testosterone bromantan
uses testosterone
uses bromantan
regulation testosterone bromantan
regulation testosterone
regulation bromantan The search query results, which consist of websites and other files (or lists of such files), may then contain information to the effect that testosterone is a steroid subject to regulated use, and that bromantan is sometimes used in attempts to hide or mask the presence of testosterone.

Once search query results are returned to the processing station 130, they can be compiled and formatted into a more compact and easy-to-read form (step 214 in FIG. 2). As a first example, the files/websites returned as search query results can be reduced in number, as by retaining only some number of the files/websites that ranked highest in relevance; by filtering the files/websites to retain only those which appear to contain more relevant content (e.g., those files/websites which contain more of the exemplary EDWs noted earlier); and/or by filtering the files/websites to eliminate files/websites which appear to contain less relevant content.

As another example, the files/websites may also be reduced in size, as by filtering and eliminating contents within the files/websites. Filtering and reduction of file contents can be performed in a variety of ways, as by removing common formatting/programming codes, control characters, and the like; by retaining only strings occurring within some proximity to one of the aforementioned EDWs; by eliminating "stop words" (extremely common words which convey little information about a topic, such as "the," "of," "and," "to," etc.); and/or by other common filtering methods.

The remaining files/websites in the search query results may then be compiled by the processing station 130, preferably by segregating search query results directed to different subjects/topics, and providing each set of results under its own heading relating to the subject/topic in question (step 216 in FIG. 2). The compiled search results can then be transmitted back to the data capture unit 100 to be shown to the user on the display 106. Expanding on the foregoing example, the display 106 might first show a heading "Possible Substances", followed by the listings of the candidate substances, their alternative/variant names, and their relative concentrations (with this last quantity often being ascertainable from the sample data). Next, the display 106 might show the heading "Uses" followed by the relevant files/websites (or portions thereof) returned as results from the "uses" search queries. Next, the heading "Regulation" might be presented, followed by the files/websites (or portions thereof) returned as results from the "regulation" search queries. Further headings and search results can be presented if searches were conducted with EDWs on other topics, e.g., "CAS," "MSDS," "formula," "properties," "standard," etc. If numerous search queries are made with EDWs related to diverse topics, the resulting report presented to the user can be long, and thus the display 106 should have the capability to index or scroll to reveal further search query results delivered by the processing station 130.

It can be useful if the user has the capability to choose the topics of the search queries generated by the processing station 130 so that the user may concentrate any information returned by the processing station 130 onto topics of particular interest. Thus, for example, the data capture unit 100 might present the user with a menu before or after capturing sample data whereby the user can select search topics of interest. For example, the user might be presented with a menu on the display 106 to select topics such as "Common and Alternative Names," "Common Uses," "Properties," "Handling and Precautions," etc. When user selects a topic, the processing station 130 can then generate search queries from the candidate substance name(s) and from any stored EDWs relating to the topic in issue. For example, a user's selection of the topic "Common and Alternative Names" might generate search queries from the candidate substance name(s) in combination with EDWs such as "IUPAC," "trade name," "trade mark," "commercial name," "name," etc. Alternatively or additionally, the user simply might be presented with a menu of the EDWs that might be used in conjunction with the candidate substance names when composing search queries, e.g., "IUPAC," "CAS," "MSDS," "formula," "properties," "standard," etc. The processing station 130 might then generate and execute search queries only in accordance with the EDWs selected by the user.

Since a possible function of the system is for field deployment of one or more users bearing data capture units 100 during crisis of public safety and/or law enforcement situations—such as during disaster response, hazardous material spills, suspected chemical/biological/nuclear attacks, inspections for contraband, and so forth—rapid and accurate identification of candidate substances, and the provision of relevant information to the user regarding these candidate substances, can be critical. In some cases, it may be necessary for the user to receive instructions from, or relay information to, a decisionmaker with higher authority, e.g., one who has the power to make decisions as to how to respond to the situation faced by the user. Thus, it is preferred that such decisionmakers also be provided in networked communication with the processing station 130, and/or directly with the data capture unit 100 (step 218 in FIG. 2). As an example, if the data capture unit 100 is deployed in a crisis situation, the decisionmaker might remotely monitor the sample data, candidate substance identification, and search query results generated by the system (perhaps in conjunction with one or more experts), and might provide instruction to the user of the data capture unit 100 in accordance with these results. Where multiple data capture units 100 are deployed in the field, the data capture units 100 might have the ability to allow their users to rank the priority/importance of sample data measurements, and thus their need for attention and oversight by decisionmakers, so that sample data measurements of greater criticality may more rapidly obtain review by decisionmakers and/or experts, and so that the user might more rapidly receive appropriate instruction.

To further illustrate possible features and uses of the system, following are additional examples of how it might be used.

EXAMPLE 1

One or more users bearing handheld (or otherwise portable) data capture units 100 seek to make in-situ measurements on samples of raw materials/feedstock, and/or on samples of processed materials or manufactured goods, in a manufacturing environment. The users capture sample data at one or more desired locations on one or more samples, and the sample data is wirelessly transmitted to one or more processing stations 130 for identification of the candidate substances within the samples, and for generation of search queries which include the names of the identified candidate substances. Here, the processing station(s) 130 may be networked to other databases/workstations 140 in a local or wide area network which is secure, owing to a desire for industrial confidentiality. The processing station(s) 130 (and/or the connected databases/workstations 140) use the sample data to execute identification of the candidate substances within the samples, as by referring to reference libraries and making use of matching/fingerprinting methods. This results in a list of names of candidate substances. These candidate substance names are then used as EDWs alone, in combination with each other, and/or in combination with other EDWs (e.g., "IUPAC," "MSDS," etc.) to generate search queries. Here, assuming a candidate substance X was identified, the processing station(s) 130 and/or user(s) might specify search queries related to the source of candidate substance X, such as one or more of "origin X," "source X," "product X," "byproduct X," "supplier X," and so forth. Alternatively or additionally, the processing station(s) 130 and/or user(s) might specify search queries related to the safety of candidate substance X, such as one or more of "hazards X," "toxicity X," "handling X," "precautions X," "MSDS X," etc. Each of these search queries can then be submitted to the secure networked databases 140, and/or to external networked databases 140 on the World Wide Web, to return search query results containing (or otherwise being relevant to) the EDWs within the search queries. These search query results may then be filtered, abstracted, or otherwise processed, and may be presented to experts, decisionmakers, and/or users as formatted reports. These formatted reports provide the identification of the candidate substance along with textual literature and other information regarding the substance, as opposed to merely providing raw sample data and/or the candidate substance name alone.

EXAMPLE 2

A user of one or more analytical instruments, each of which bears a sensor 102 for capturing sample data, wishes to analyze a sample in a standard laboratory environment. The sample data is sent to personal computers in wired or wireless communication with the instruments, and is in turn sent to a central processing station 130 for identification of the candidate substances within the samples. The processing station 130 processes the sample data and identifies a primary candidate substance X therein, as well as candidate substances Y and Z, which are present in lesser amounts. If one or more of candidate substances Y and Z are not identified with sufficient confidence, the processing system might provide suggestions for obtaining more definite sample data, and/or it might obtain expert feedback and/or search query results regarding verification of candidate substances, etc. The final candidate substance names can then be used by the processing station 130 alone, in combination with each other, and/or in combination with other EDWs to formulate search queries such as "X Y Z," "mixture X Y Z," "X Y Z indicates," "X Y Z symptoms," "hazards X Y Z," and so forth. Subsequent search query results may then be filtered, abstracted, or otherwise processed, and may be presented to experts, decisionmakers, and/or users as formatted reports. Again, these formatted reports provide the identification of the candidate substance along with textual literature and other information regarding the substance, as opposed to merely providing raw sample data and/or the candidate substance name alone.

It should be understood that the EDWs noted in prior discussions are merely exemplary, and numerous different EDWs not noted in this document could also or alternatively be used, with examples including "acid value"; "atomic properties"; "boiling point"; "burning rate"; "chemical formulae"; "chemical resistance"; "coefficient of expansion"; "color"; "commercial products using"; "compressive modulus"; "conductivity"; "density"; "dielectric constant"; "dielectric strength"; "electrical properties"; "enthalpy"; "flash point"; "freezing point"; "functional groups in"; "hardness"; "heat of fusion"; "heat of sublimation"; "heat of vaporization"; "impact strength"; "industrial uses"; "iodine value"; "isotopes"; "magnetic properties"; "manufacturing process to produce"; "mechanical properties"; "melting point"; "microwave properties"; "molecular structure"; "molecular weight"; "nuclear properties"; "pH"; "physical properties"; "pK values"; "refractive index"; "resistance"; "saponification value"; "solubility properties"; "specific gravity"; "specific heat"; "suitable solvents for"; "tensile strength"; "thermal conductivity"; "thermal properties"; "UV cutoff"; and "viscosity." If the user or system seek information on topics not noted in this document, EDWs relevant to these topics could be formulated and used. It should also be understood that the EDWs noted in this document (or other EDWs) can readily be replaced with equivalent terms having the same or similar meanings; for example, in place of "toxicity," EDWs having similar meanings such as "poison," "noxious," etc. could be used. Further, EDWs may vary in form, e.g., between noun and adjective forms, plural and singular forms, etc., and all such forms are essentially equivalent. In this respect, the form of an EDW will often be irrelevant because many search engines perform "stemming"—that is, they remove plural endings (such as "s"), remove past/present participle endings (such as "ed" and "ing"), and otherwise "stem" terms to reduce them to "rootwords" on which further search steps are based.

Additionally, while the foregoing discussion generally contemplates the capture of sample data by the data capture unit 100, and the delivery of related search query results to the user on the display 106, in rapid succession, this need not necessarily be the case. For example, the data capture unit 100 might collect several sets of sample data before delivering this sample data to the processing station 130 and obtaining search query results in return. As another example, the data capture unit 100 might store sample data on a removable memory, with the removable memory later being removed and subsequently attached in communication with the processing station 130. The resulting search query results could then be wirelessly uploaded to the data capture unit 100, or written onto the removable memory for subsequent reloading onto the data capture unit 100. If the search query results are no longer needed by the user in the field, the search query results might simply remain at the processing station 130 without being transmitted to the data capture unit 100 and user. It is notable that in situations where the sensors 102 used to collect sample data are stationary, remote, and/or numerous—as in the foregoing example of multiple sensors 102 situated along a fence line or boundary—there may be no need to deliver search query results back to the sensors 102, and instead the search query results can simply be provided to the processing station 130, at which a user/operator may be monitoring the sensors 102. Despite the foregoing, the ability to obtain search query results in the field rapidly after the sample data are collected is a particularly preferred and useful feature of the invention.

As processing capabilities grow and costs decrease, it may also be possible to incorporate the functionality provided by the processing station 130 directly within the data capture unit 100. For example, the data capture unit 100 might perform sample data capture and also perform identification of the candidate substances within the sample, and might thereafter communicate with the processing station 130 to generate the search queries and collect and return search query results. It may ultimately be possible to eliminate the processing station 130 altogether—that is, the data capture unit 100 might itself perform candidate substance identification from the sample data, generate search queries and deliver them to databases 140 and/or experts, and compile and present search query results to the user.

It should be understood that the versions of the invention described above are merely exemplary, and the invention is not intended to be limited to these versions. Rather, the scope of rights to the invention is limited only by the claims set out below, and the invention encompasses all different versions that fall literally or equivalently within the scope of these claims.

What is claimed is:

1. A molecular spectrometry system including:
    a. a sensor capturing wavelength data from a sample;
    b. a processing station configured for:
       (1) receiving the wavelength data from the sensor,
       (2) generating substance data from the wavelength data, the substance data at least partially identifying one or more substances;
       (3) networking to provide reliability feedback to the user with respect to matching/fingerprinting efforts and provide suggestions to the user to obtain more reliable/definite sample data;
       (4) generating one or more search queries from the substance data;
       (5) providing the search queries to a network of databases, wherein at least some of the databases contain information about the properties of substances; and
       (6) receiving the search query results, the search query results containing at least some of the information from the networked databases about the properties of the substances to which the substance data relate.

2. The molecular spectrometry system of claim 1 wherein the sensor wirelessly communicates the wavelength data to the processing station.

3. The molecular spectrometry system of claim 1 wherein:
    a. the sensor includes a display,
    b. the sensor:
       (1) receives at least some of the search query results from the processing station, and
       (2) displays these search query results on the display.

4. The molecular spectrometry system of claim 1 wherein:
    a. the sensor includes:
       (1) a wireless receiver, and
       (2) a display,
    b. the sensor:
       (1) wirelessly receives at least some of the search query results from the processing station, and
       (2) displays these search query results on the display.

5. The molecular spectrometry system of claim 1 wherein:
    a. the sensor includes a camera, and
    b. the camera captures an image of the sample at or near the time when the sensor captures wavelength data from the sample.

6. The molecular spectrometry system of claim 1 wherein the sensor is provided on a portable data capture unit, the data capture unit further including:
    a. a wireless transmitter transmitting the wavelength data to the processing station;
    b. a wireless receiver receiving at least some of the search query results from the processing station; and
    c. a display providing a visual representation of the search query results received from the processing station.

7. The molecular spectrometry system of claim 6 wherein:
    a. the sensor further includes a camera, wherein the camera captures an image of the sample;
    b. the wireless transmitter transmits the image to the processing station;
    c. the processing station provides the image to at least one user in networked communication with the processing station.

8. The molecular spectrometry system of claim 7 wherein the processing station also provides at least some of the search query results to the user in networked communication with the processing station.

9. The molecular spectrometry system of claim 1 wherein the processing station, after receiving the search query results, filters the search query results by one or more of:
    a. discarding search query results which include certain terms predefined within the processing station;
    b. discarding search query results which fail to include certain terms predefined within the processing station.

10. The molecular spectrometry system of claim 9 wherein the search query results are transmitted to the sensor after being filtered.

11. The molecular spectrometry system of claim 1 wherein the networked databases are provided on the World Wide Web.

12. The molecular spectrometry system of claim 1 wherein the networked databases include at least some websites on the World Wide Web having website addresses predefined within the processing station.

13. The molecular spectrometry system of claim 1 wherein the search queries are generated from the substance data by adding one or more words thereto.

14. The molecular spectrometry system of claim 1 wherein the search queries are generated from the substance data by adding at least one of the following words thereto:
   a. IUPAC;
   b. CAS;
   c. formula;
   d. properties;
   e. standard;
   f. reference;
   g. uses;
   h. suppliers;
   i. commercial;
   j. trade name;
   k. MSDS;
   l. toxicity;
   m. hazard;
   n. measurement;
   o. regulation;
   p. ultraviolet spectrum;
   q. near infrared spectrum;
   r. infrared spectrum;
   s. Raman spectrum;
   t. NMR spectrum;
   u. microwave spectrum;
   v. X-ray spectrum;
   w. terahertz spectrum; and
   x. mass spectrum.

15. The molecular spectrometry system of claim 1 wherein:
   a. at least three search queries are generated from the substance data, each search query being generated by adding at least one of the following words thereto:
      (1) IUPAC;
      (2) CAS;
      (3) formula;
      (4) properties;
      (5) standard;
      (6) reference;
      (7) uses;
      (8) suppliers;
      (9) commercial;
      (10) trade name;
      (11) MSDS;
      (12) toxicity;
      (13) hazard;
      (14) measurement;
      (15) regulation;
      (16) ultraviolet spectrum;
      (17) near infrared spectrum;
      (18) infrared spectrum;
      (19) Raman spectrum;
      (20) NMR spectrum;
      (21) microwave spectrum;
      (22) X-ray spectrum;
      (23) terahertz spectrum; and
      (24) mass spectrum;
   b. providing the search query results to the sensor, with the search query results of each search query being segregated from the search query results of any other search queries.

\* \* \* \* \*